(12) United States Patent　(10) Patent No.: US 12,257,700 B2
Kadokura et al.　(45) Date of Patent: Mar. 25, 2025

(54) CONSTRAINT MECHANISMS, SYSTEMS, AND METHODS

(71) Applicant: INTUITIVE SURGICAL OPERATIONS, INC., Sunnyvale, CA (US)

(72) Inventors: Grant M. Kadokura, San Diego, CA (US); Andrew C. Waterbury, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/318,360

(22) Filed: May 16, 2023

(65) Prior Publication Data

US 2023/0286179 A1　Sep. 14, 2023

Related U.S. Application Data

(62) Division of application No. 16/776,753, filed on Jan. 30, 2020, now Pat. No. 11,691,299.

(60) Provisional application No. 62/800,012, filed on Feb. 1, 2019.

(51) Int. Cl.
　　*B25J 18/00*　　(2006.01)
　　*F16H 19/00*　　(2006.01)

(52) U.S. Cl.
　　CPC ............ *B25J 18/00* (2013.01); *F16H 19/005* (2013.01); *F16H 2019/008* (2013.01)

(58) Field of Classification Search
　　CPC ....... B25J 18/00; G05G 5/04; F16H 2035/006
　　See application file for complete search history.

(56) References Cited

U.S. PATENT DOCUMENTS

| | | |
|---|---|---|
| 3,012,447 A | 12/1961 | Wallace |
| 3,147,629 A | 9/1964 | Michalec |
| 3,662,610 A | 5/1972 | Thoen |
| 4,609,841 A | 9/1986 | Masaki et al. |
| 5,771,753 A | 6/1998 | Kwon et al. |
| 8,852,208 B2 | 10/2014 | Gomez et al. |
| 9,295,524 B2 | 3/2016 | Schena et al. |
| 9,358,074 B2 | 6/2016 | Schena et al. |
| 9,803,732 B2 | 10/2017 | Rinke |
| 2014/0128886 A1 | 5/2014 | Holop et al. |
| 2018/0079090 A1 | 3/2018 | Koenig et al. |
| 2020/0246983 A1 | 8/2020 | Kadokura et al. |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Jake Cook

(74) *Attorney, Agent, or Firm* — JONES ROBB, PLLC

(57) ABSTRACT

A tool includes a transmission mechanism, a shaft, and a rotary device. The shaft is rotatable with reference to the transmission mechanism through a defined range of rotational motion about a first axis of rotation and includes a protrusion extending from the shaft in a direction normal to the first axis of rotation. The rotary device includes a first stop surface, a second stop surface, and a notch between the first stop surface and the second stop surface, with the notch configured to receive the protrusion extending from the shaft. Rotation of the shaft through a midpoint of the range of rotational motion causes the protrusion to enter the notch of the rotary device and rotate the rotary device from a first position to a second position.

15 Claims, 12 Drawing Sheets

CONSTRAINT MECHANISMS, SYSTEMS, AND METHODS

CROSS-REFERENCE TO APPLICATIONS

This application is a divisional application of U.S. application Ser. No. 16/776,753, filed Jan. 30, 2020, which claims the benefit of priority to U.S. Provisional Application No. 62/800,012, filed Feb. 1, 2019, each of which is incorporated by reference herein in its entirety.

TECHNICAL FIELD

Aspects of the present disclosure relate to rotation constraint mechanisms for various tools, such as surgical instruments.

INTRODUCTION

Various tools, such as surgical instruments, can be configured with multiple degrees of freedom of movement, such as articulation of joints, rotation of shafts, or other movements. Some tools include a main shaft that generally extends from a transmission mechanism to a proximal end of the shaft to an end effector at a distal end of the shaft. The transmission mechanism can include various components configured to actuate movement of the tool, such as, for example, actuating an end effector, manipulating one or more joints, and rotating a shaft of the tool. In some cases, such movement must be constrained to a certain predefined range of rotational motion, due to, e.g., constraints of the mechanism actuating the movement. Further, such motions may be constrained to maintain accurate encoding of the position of such components. In addition, tools such as surgical instruments can exhibit relatively high levels mechanical complexity and can also be subject to significant packaging constraints. Thus, the space available for constraint mechanisms may be limited.

A need exists for constraint mechanisms that do not occupy excessive space within a tool, provide reliable movement restriction of ranges of motion of the tool, and cannot be unintentionally activated.

SUMMARY

Embodiments of the present disclosure may solve one or more of the above-mentioned problems and/or may demonstrate one or more of the above-mentioned desirable features. Other features and/or advantages may become apparent from the description that follows.

In accordance with at least one embodiment, a tool includes a transmission mechanism, a shaft rotatable relative to the transmission mechanism, and a stop mechanism associated with the shaft, the stop mechanism being transitionable between a first state and a second state. In the first state, the shaft is free to rotate in a first direction and in a second direction opposite to the first direction. In the second state, the shaft is constrained from rotating in one of the first direction or the second direction by a defined first endpoint of a range of rotational motion of the shaft.

In accordance with at least another embodiment, a tool includes a transmission mechanism, a shaft, and a rotary device. The shaft is rotatable with reference to the transmission mechanism through a defined range of rotational motion about a first axis of rotation, and includes a protrusion extending from the shaft in a direction normal to the first axis of rotation. The rotary device includes a first stop surface, a second stop surface, and a notch between the first stop surface and the second stop surface. The notch is configured to receive the protrusion extending from the shaft. Rotation of the shaft through a midpoint of the range of rotational motion causes the protrusion to enter the notch of the rotary device and rotate the rotary device from a first position to a second position.

In accordance with yet another embodiment, a method of constraining rotational range of a tool shaft of a tool includes rotating the shaft through a range of rotational motion in a first direction and moving a stop mechanism from a first position to a second position by engaging the stop mechanism with a protrusion extending from the shaft during rotation of the shaft through a midpoint of the range of rotational motion.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

The present disclosure contemplates various embodiments of rotational stop mechanisms that constrain rotation of components of a tool, such as a shaft of a surgical instrument, within a predefined range of rotational motion. In accordance with the present disclosure, stop mechanisms can exhibit a first state in which rotational motion of the component is permitted in two rotational directions, and a second state in which rotation of the component is constrained in one of the two rotational directions. Movement of the tool component through a predetermined rotational position changes the stop mechanism from the first state to the second state. Stop mechanisms of the present disclosure can further exhibit a third state in which rotational motion of the component is constrained in only the other of the two rotational directions.

Various embodiments of rotational constraint devices of the present disclosure include a rotary device with features configured to interface with one or more complementary features of the rotational component of the tool. In certain embodiments of the disclosure, stop mechanisms optionally include rotary devices that rotate in a direction counter to the direction of rotation of the shaft of the tool, for example, and include one or more features configured to interface with one or more features on the rotating component of the tool, such as the tool shaft. Stop mechanisms according to the present disclosure generally occupy less space circumferentially around the rotating shaft of the tool than other devices for constraining motion. For example, other solutions for constraining rotation of the shaft, such as a collar with one or more inner and outer stop tabs that ride in respective annular grooves in the rotating component and a structure surrounding the rotating component, or a ball bearing that rides in similar grooves, require a structure that entirely surrounds the shaft. In contrast, structures in accordance with the present disclosure do not require a circumferentially surrounding structure and, therefore, portions of the tool can be made smaller in overall diameter compared to other solutions.

In embodiments of the disclosure, the rotary device rotates about an axis parallel to, and offset from, an axis of rotation of the rotatable component of the tool. In other embodiments of the disclosure, the rotary device can be configured to rotate about an axis perpendicular to the axis of rotation of the rotatable component and include similar features and functionality to embodiments in which the rotatable component rotates about an axis parallel to the axis of rotation of the rotatable component.

Figure 1:
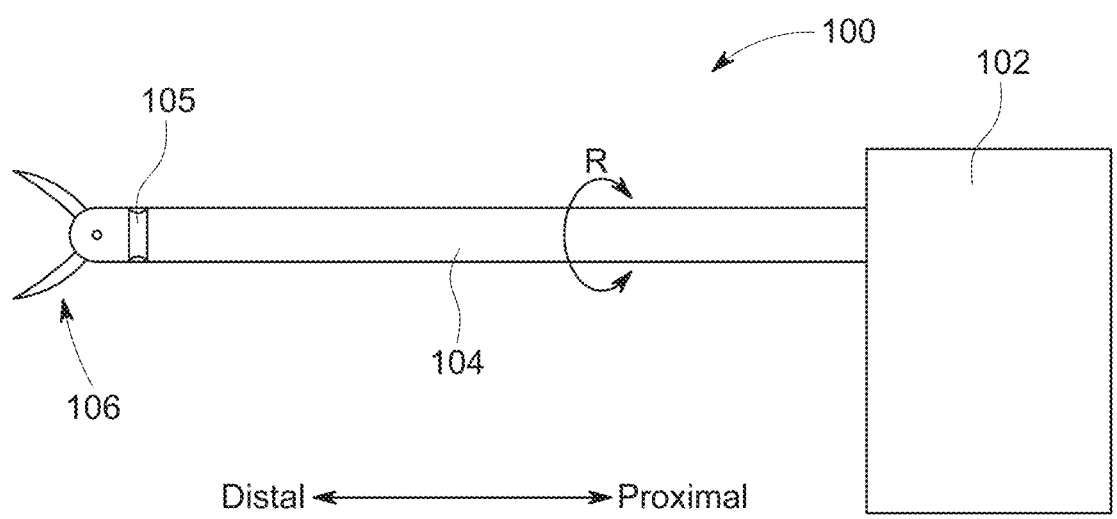
FIG. 1 is a schematic view of an embodiment of a surgical instrument according to the present disclosure.

Referring now to FIG. 1, a schematic representing an embodiment of a tool 100 (such as, for example, a surgical instrument) is shown. While aspects of the present disclosure are discussed in the context of surgical instruments, embodiments of the present disclosure can be used with various tools other than surgical instruments. The tool 100 includes a transmission mechanism 102 configured to interface with a manipulating system, such as manipulating systems 700 or 800 shown below in connection with FIGS. 7 and 8, respectively. A shaft 104 extends distally from the transmission mechanism 102. An end effector 106 is coupled to the distal end of the shaft 104. In some embodiments, the end effector 106 can optionally be coupled to the shaft 104 by one or more articulating joints 105 that provide one or more degrees of freedom of articulation of the end effector 106 relative to the shaft 104. In embodiments, operation of the end effector 106 and articulation of the one or more articulating joints 105 is controlled by the manipulating system (e.g., manipulating system 700 or 800) through the transmission mechanism 102, which includes various mechanical and/or electromechanical devices that transmit motion, energy, and/or signals from the manipulating system to the end effector 106 and/or the one or more articulating joints 105.

Figure 2:
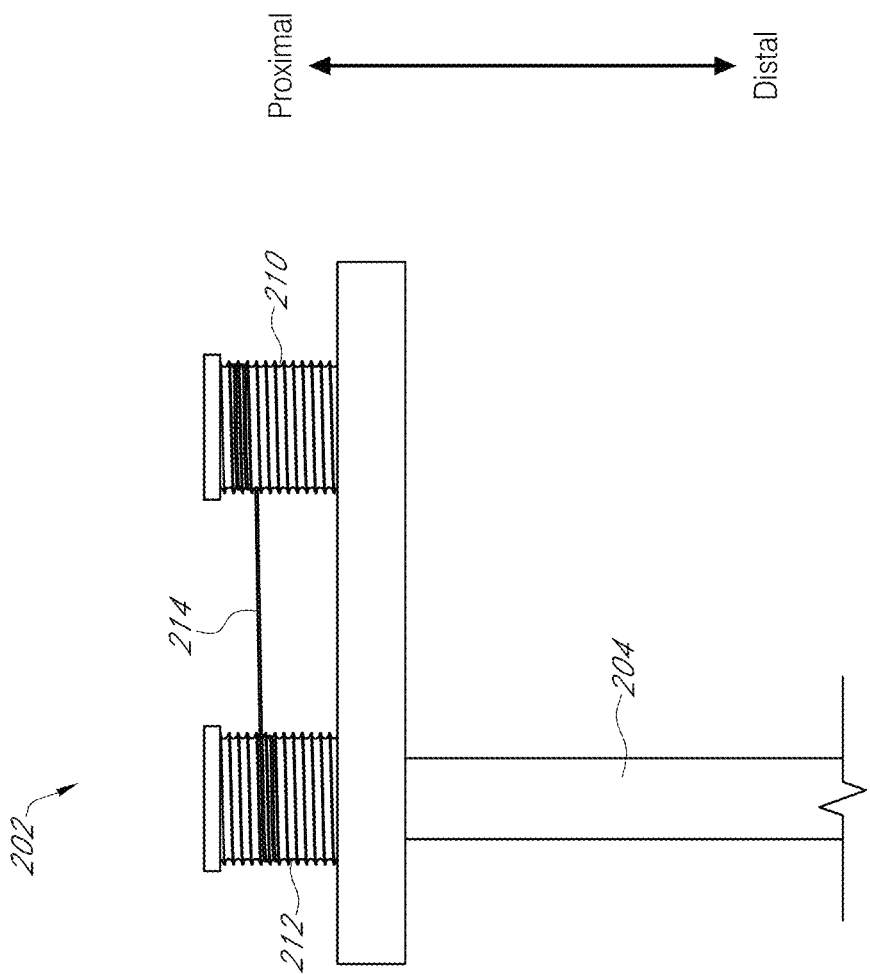
FIG. 2 is a side schematic view of an embodiment of a surgical instrument according to the present disclosure.

In embodiments of the present disclosure, the transmission mechanism 102 is configured to impart a roll motion to the shaft 104 of the tool 100 (see, e.g., arrow R depicting rotation of shaft 104 around its longitudinal axis). In embodiments, a total roll motion of the shaft 104 must be constrained within a predetermined range of rotational motion to ensure consistent functioning and potentially to avoid damage to components of the transmission mechanism. For example, referring now to FIG. 2, in various embodiments, a transmission mechanism 202 is configured to rotate a shaft 204 through a system including a capstan 210, a pulley 212 coupled with the shaft 204, and at least one drive cable 214 coupled between the capstan 210 and the pulley 212. In the embodiment of FIG. 2, the capstan 210 is operably coupled to a motor or other drive device (not shown) in the manipulating system (e.g., manipulating system 700 or 800) when the tool 100 (FIG. 1) is installed on the articulating system.

In some embodiments, such as that of FIG. 2, the at least one drive cable 214 is attached at a first end to the capstan 210 and at a second end to the pulley 212. The at least one drive cable 214 can optionally be wrapped at least partially around the capstan 210 and the pulley 212. As the capstan 210 is rotated by the drive device, the at least one drive cable 214 pays in or out from the capstan 210, rotating the pulley 212 and the shaft 204. Optionally, the at least one drive cable 214 comprises two drive cables, each wrapped in an opposite direction around the capstan 210 and pulley 212 to enable rotation of the pulley 212 and shaft 204 in either of two rotational directions. Because the at least one drive cable is not endless (i.e., not in the form of a belt) and is connected at each end to the capstan 210 and the pulley 212, respectively, the shaft 204 is not capable of continuously rotating as would be possible with a belt-type arrangement. Further, it may be desired to encode the position of the shaft 204 and provide position information to a user through an interface of the articulating system.

Accordingly, embodiments of the disclosure include mechanisms configured to constrain rotation of the shaft between known rotational endpoints. Various embodiments of rotational constraint devices of the present disclosure include a rotary device with features configured to interface with one or more complementary features of the shaft. As the shaft rotates, the one or more complementary features of the shaft interact with the rotary device to rotate the rotary device between various positions.

Figure 3:
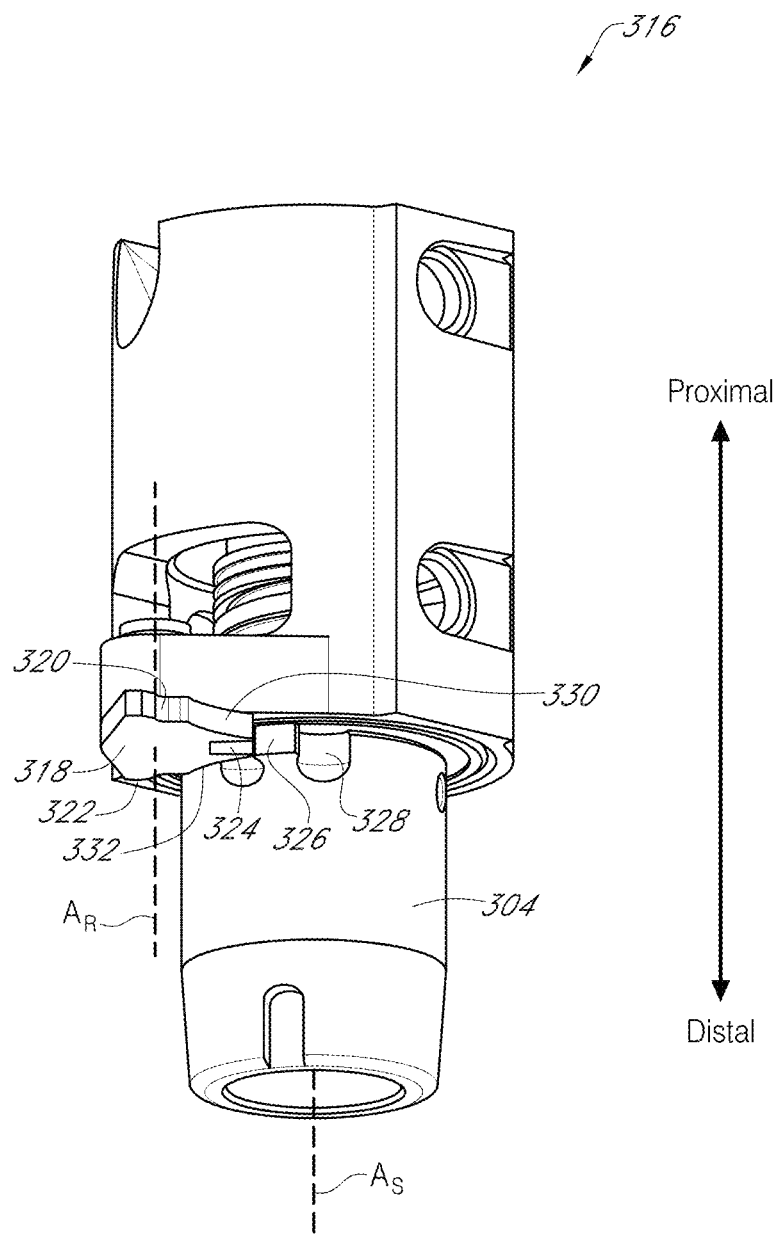
FIG. 3 is a perspective view of an embodiment of a stop mechanism according to the present disclosure.

For example, referring now to FIG. 3, a perspective view of a rotational constraint mechanism 316 according to an embodiment of the present disclosure is shown. The rotational constraint mechanism includes a rotary device 318 with a rotational axis AR oriented parallel to and offset from a rotational axis $A_s$ of a shaft portion 304. The rotary device 318 includes a first stop surface 320, a second stop surface 322, and a notch 324 between the first stop surface 320 and the second stop surface 322. Between the first stop surface 320 and the notch 324 is a first profiled portion 330, and a second profiled portion 332 is between the notch 324 and the second stop surface 322. Each of the first and second profiled portions 330 and 332 can optionally feature a profile that is complementary to a partial profile of the shaft portion 304, as discussed further below. The shaft portion 304 includes a protrusion 326 extending from the shaft portion 304 normal to the rotational axis $A_s$ of the shaft portion 304. Recesses 328 are positioned on either side of the protrusion 326 to facilitate rotation of the rotary device 318 by allowing portions of the rotary device 318 around the notch 324 to enter the recesses 328 as the rotary device rotates.

Figure 4A:
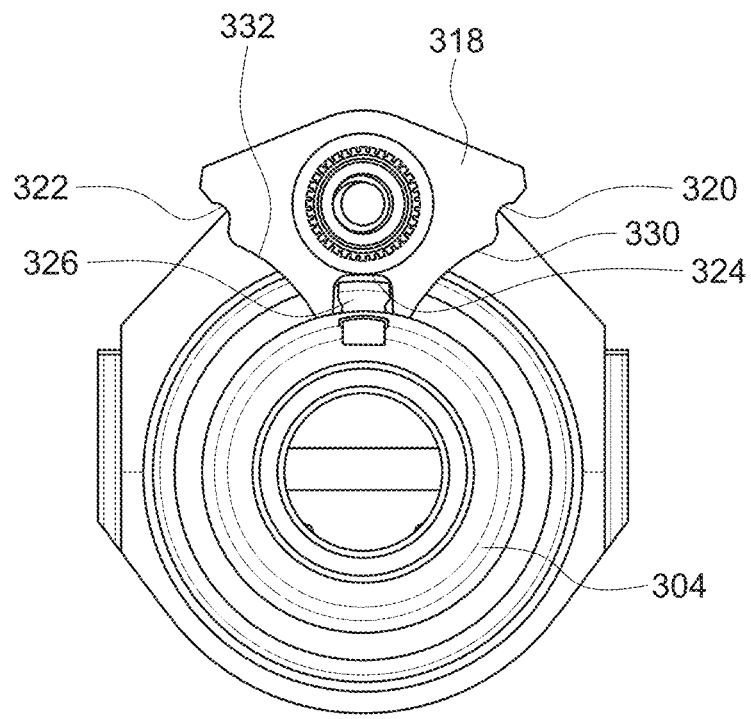
FIGS. 4A-4E are cross sectional views of the stop mechanism according to the embodiment of FIG. 3.

Referring now to FIGS. 4A-4E, the rotational constraint mechanism 316 according to the embodiment of FIG. 3 is shown in an end view in various states. In FIG. 4A, the rotary device 318 is in a center position. The shaft portion 304 is also in a center position, i.e., at a rotational midpoint between endpoints of the rotational range of rotational motion of the shaft portion 304. In this position, the protrusion 326 is positioned within the notch 324 of the rotary device 318. The position shown in FIG. 4A can be referred to as a first state in which the shaft portion 304 is free to rotate in either the clockwise or counter-clockwise directions.

Figure 4B:
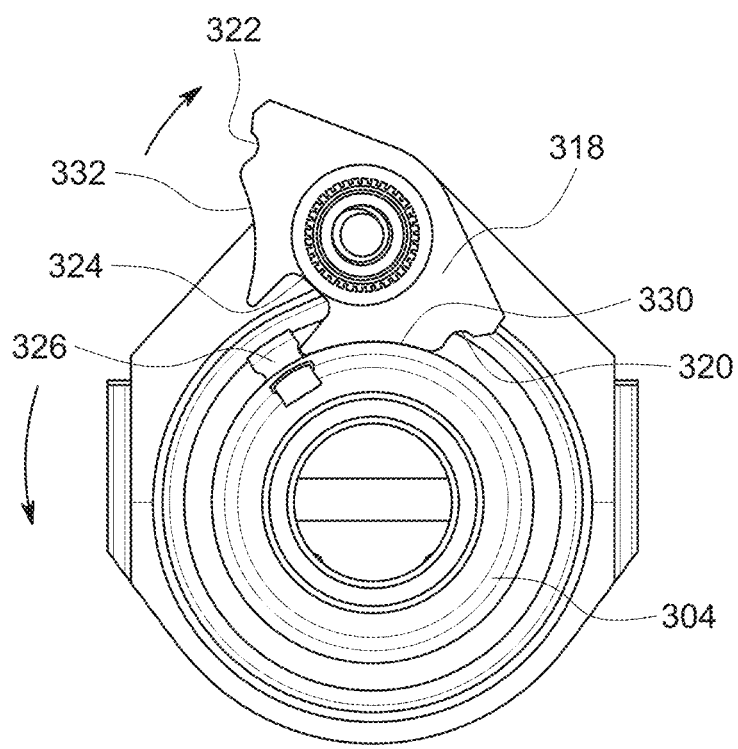

As the shaft portion 304 begins turning counter-clockwise, as shown in the view of FIG. 4B, the protrusion 326 bears against an interior surface of the notch 324 and turns the rotary device 318 clockwise until the protrusion 326 exits the notch 324. In this position of the rotary device 318, the first profiled portion 330 rests against the outer surface of the shaft portion 304. In certain embodiments, the first profiled portion 330 can have a radiused profile having a radius of curvature equal to the radius of the shaft portion 304. This configuration maintains the position of the rotary device 318 relative to the shaft portion 304 as the shaft portion 304 continues to rotate counter-clockwise.

As the shaft portion 304 turns counter-clockwise beyond the position shown in FIG. 4B, the protrusion 326 eventually contacts the first stop surface 320 of the rotary device 318. Mechanical interference between the protrusion 326 and the rotary device 318 at the first stop surface 320 prevents further rotation of the shaft portion 304 in the counter-clockwise direction, and the shaft portion 304 has reached a constrained orientation in which rotation in one direction (i.e., the counter-clockwise direction as viewed in FIG. 4C) is prevented. In other words, in the position shown in FIG. 4C, rotation of the shaft portion 304 is constrained to a maximum rotation in at least one rotational direction (i.e., the counter-clockwise direction). The position shown in FIG. 4C can be referred to as a second state, in which rotation of the shaft portion 304 is constrained to a maximum rotation in one rotational direction.

Figure 4C:
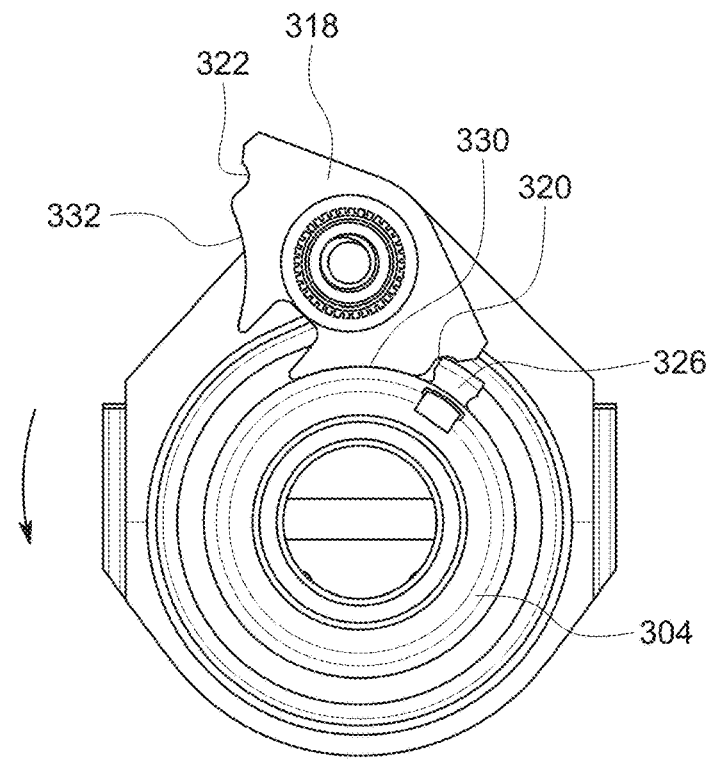
Figure 4D:
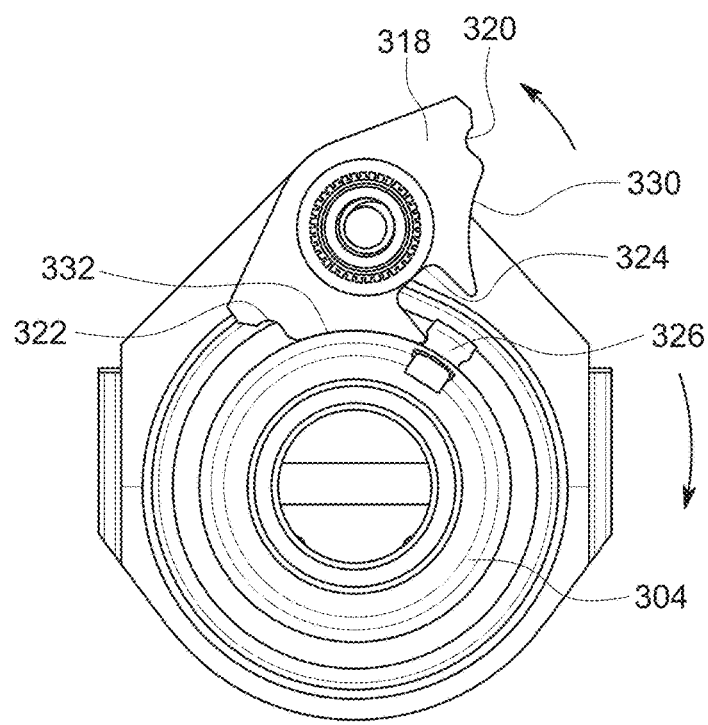
Figure 4E:
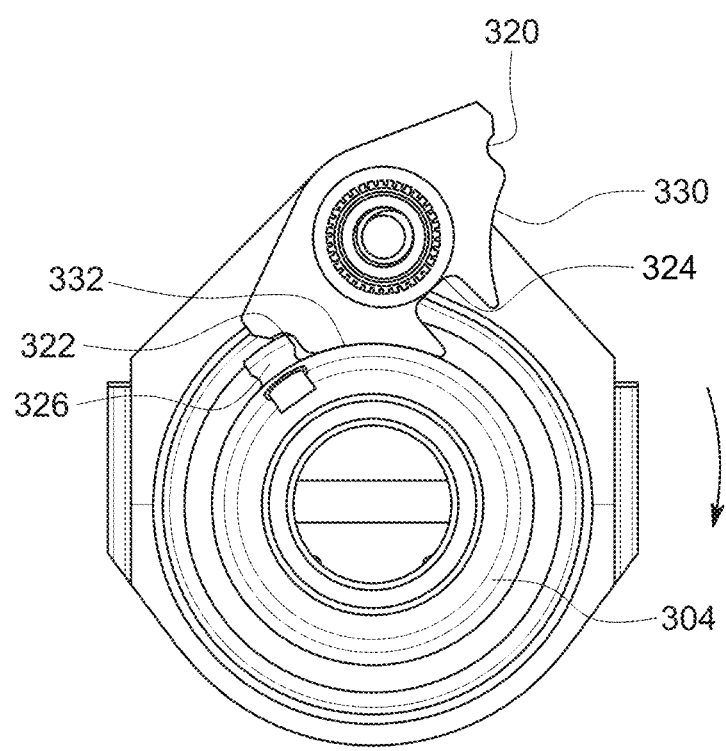

A clockwise rotation of the shaft portion 304 from the orientation shown in FIG. 4C returns the shaft portion 304 and the rotary device 318 to the configuration shown in FIG. 4A. Rotating the shaft portion 304 clockwise further from the FIG. 4A position results in the protrusion 326 exiting the notch 324, and the rotary device 318 rotates counter-clockwise to the position shown in FIG. 4D. The second profiled portion 332 rests against the shaft portion 304, and the rotary device 318 maintains this position while the shaft portion 304 is rotated further clockwise to the position shown in FIG. 4E. In the position of FIG. 4E, the protrusion 326 contacts the second stop surface 322, and the shaft portion 304 is prevented from turning further in the clockwise direction. In other words, in the position of FIG. 4E, rotation of the shaft portion 304 is constrained from rotating further in the clockwise direction. The position of FIG. 4E can be referred to as a third state of the stop mechanism, in which rotation of the shaft portion 304 is constrained to a maximum rotation in the other of the two rotational directions as compared to the second state.

A total distance of rotation between rotational endpoints depends on the configuration of the protrusion 326 and the rotary device 318. In the embodiment of FIGS. 4A-4E, a total distance of rotation between the position shown in FIG. 4C and the position shown in FIG. 4E can be nearly 720 degrees (two full rotations), such as, for example, 1.5 revolutions (540 degrees) or more, 1.75 revolutions (630 degrees) or more, 690 degrees, or more. Lesser or greater amounts of rotation are within the scope of the disclosure.

Figure 5:
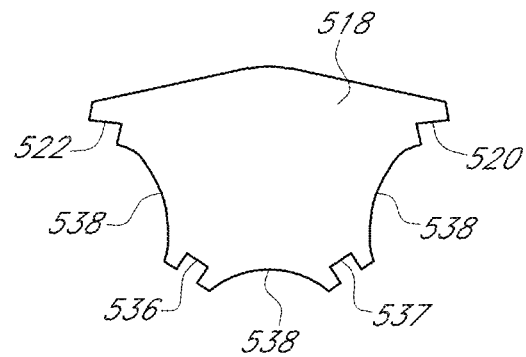
FIG. 5 is a schematic view of a rotary component of a stop mechanism according to another embodiment of the disclosure.

Rotations greater than two rotations (720 degrees) are possible by increasing the number of notches and profiled portions of the rotary device. For example, referring now to FIG. 5, a rotary device 518 according to another embodiment includes two notches 536, 537 positioned between first and second stop surfaces 520 and 522. Three profiled portions 538 are arranged between the first stop surface and the notch 536, between the notches 536, 537, and between the notch 537 and the second stop surface 522. Function of the rotary device 518 is similar to that of the rotary device 318 shown in FIGS. 4A-4E, but a protrusion (such as protrusion 326 in FIGS. 3 and 4A-4E) passes through both notches 536, 537 between stop surfaces 520 and 522, and the rotary device 518 thereby permits a rotational range of rotational motion of greater than two rotations (720 degrees) and can be nearly three rotations (1080 degrees). Greater rotational ranges are possible by further increasing the number of notches and profiled portions, such as 3 notches, 4 notches, 5 notches, etc. Each additional notch and associated profile surface positioned therebetween provides an additional single rotation (i.e., 360 degrees) to the total range of rotational motion.

Figure 6A:
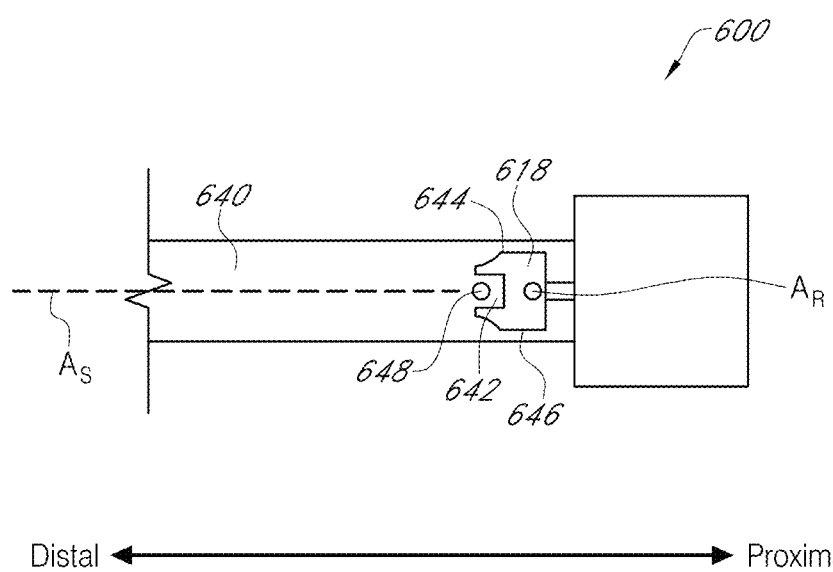
FIGS. 6A-6C are schematic top views of a tool with a stop mechanism according to another embodiment of the present disclosure.
Figure 6B:
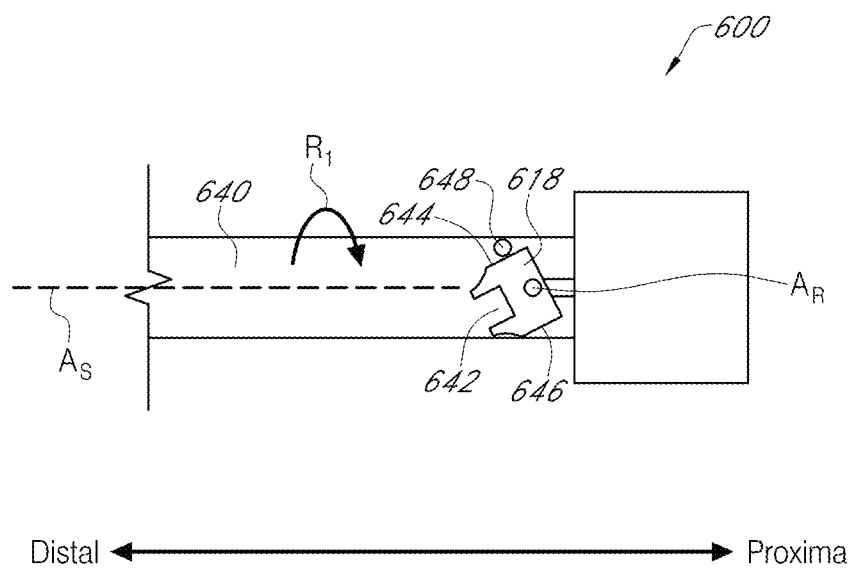
Figure 6C:
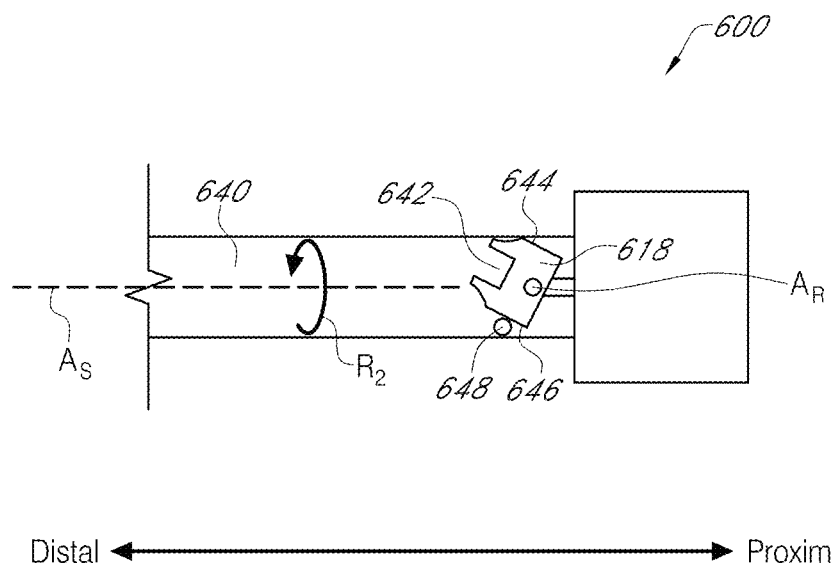

Referring now to FIGS. 6A-6C, another embodiment of a tool 600 including a rotation stop mechanism is shown in top view. Functionally the embodiment of FIGS. 6A-6C is similar to the embodiments of FIGS. 3 and 4A-4E, but in the embodiment of FIGS. 6A-6C, a rotational axis AR of a rotary device 618 is perpendicular to a rotational axis $A_S$ of a tool shaft 640. The rotational axis of the rotary device 618 is fixed relative to the tool shaft 640. The rotary device 618 includes a notch 642 and first and second stop surfaces 644 and 646. The tool shaft 640 includes a protrusion 648. In a central orientation, as shown in FIG. 6A, the protrusion 648 is positioned within the notch 642 of the rotary device 618, and the rotary device 618 is in a centered orientation. As the tool shaft 640 rotates in direction $R_1$ to the orientation shown in FIG. 6B, the protrusion 648 pushes the rotary device 618 away from the centered orientation. As the tool shaft 640 continues to rotate, the protrusion 648 contacts the first stop surface 644. The rotary device 618 is limited in rotational range, e.g., by contact with another component of the tool 600, as shown in FIG. 6B. Once the protrusion 648 contacts the stop surface 644 and the rotary device 618 is constrained from further rotation, e.g., by contact with another component of the tool 600 as shown in FIG. 6B, the tool shaft 640 is constrained from further rotation in direction $R_1$. The tool shaft 640 is free to rotate in a direction opposite $R_1$, and as shown in FIG. 6C, if the tool shaft 640 is rotated in direction $R_2$, the protrusion 648 returns to the notch 742 in the rotary device 618, and moves the rotary device 618 from the orientation shown in FIG. 6B to the orientation shown in FIG. 6C, in which further rotation of the rotary device 618 is constrained by contact between the rotary device 618 and a portion of the tool 600. Continued rotation of the tool shaft 640 in direction $R_2$ results in the protrusion 648 contacting second stop surface 646, and, because rotation of the rotary device 618 is constrained, the tool shaft 640 is prevented from rotating further in direction $R_2$.

Optionally, the rotary device 618 can include a contoured portion that matches the profile of the tool shaft 640 and prevents the rotary device 618 from rotating back to the central orientation shown in FIG. 6A. For example, the rotary device 618 can include portions analogous to the first and second profiled portions 330 and 332 discussed in connection with the rotary device 318 of FIGS. 3 and 4A-4E.

Figure 10:
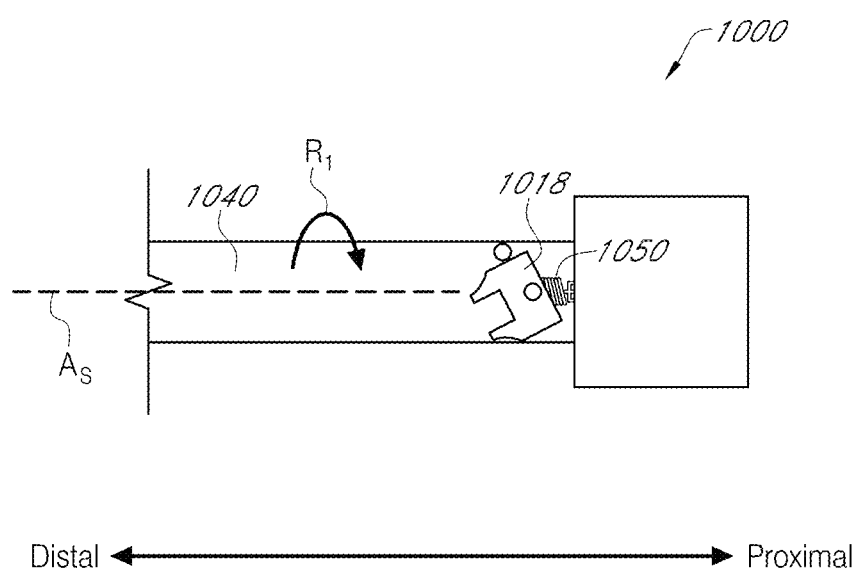
FIG. 10 is a top view of another embodiment of a tool with a stop mechanism according to an embodiment of the present disclosure.

Additionally, or alternatively, the tool 600 can include a biasing element that biases the rotary device 618 to one of the two positions shown in FIG. 6B and FIG. 6C. For example, as shown in FIG. 10, a tool 1000 includes components similar to the tool 600 described in connection with FIGS. 6A-6C, such as a tool shaft 1040 and a rotary device 1018, and also includes a biasing element 1050 that biases the rotary device 1018 to an over-center position, such as the position shown in FIG. 10. Likewise, when the shaft 1040 is rotated such that the rotary device 1018 is in the position shown in FIG. 6C, the biasing element 1050 provides a biasing force that holds the rotary device 1018 in the position corresponding to the position of FIG. 6C. The biasing element 1050 can be or include, for example, an extension spring or other resilient member, and can comprise a metal such as stainless steel or other alloy, a polymer, a composite material, or other material.

Figure 9:
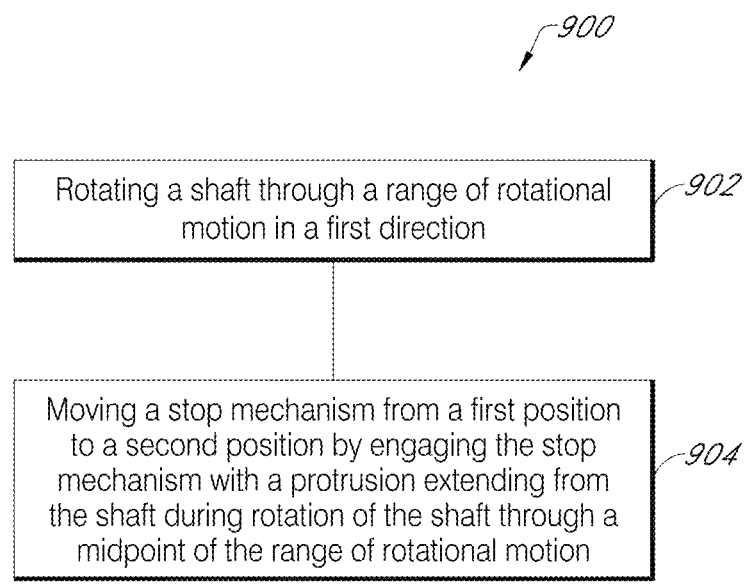
FIG. 9 is a flow chart showing a workflow for constraining rotational range of a tool shaft of a tool according to an embodiment of the present disclosure.

Referring now to FIG. 9, a flow chart showing a workflow 900 for constraining rotational range of a tool shaft of a tool is shown. At 902, the workflow includes rotating a shaft through a range of rotational motion in a first direction. At 904 the workflow includes, moving a stop mechanism from a first position to a second position by engaging the stop mechanism with a protrusion extending from the shaft during rotation of the shaft through a midpoint of the range of rotational motion.

Optionally, and not shown in workflow 900, such a workflow can further include continuing to rotate the shaft in the first direction until the protrusion engages the stop mechanism while the stop mechanism is in the second position, which prevents further rotation of the shaft in the first direction and indicates the shaft has reached a first endpoint of the range of rotational motion. Further optionally, a workflow can include rotating the shaft in a second direction opposite the first direction and moving the stop mechanism from the first position to a third position by engaging the stop mechanism with the protrusion extending from the shaft during rotation of the shaft, in the second direction, through the midpoint of the range of rotational motion. Such a workflow can also optionally include continuing to rotate the shaft in the second direction until the protrusion engages the stop mechanism while the stop mechanism is in the third position, which prevents further rotation of the shaft in the second direction and indicates the shaft has reached a second endpoint of the range of rotational motion.

Embodiments of the disclosure provide rotation stop mechanisms that provide reliable constraints on the rotational motion of the tool shaft without occupying excess space around the circumference of the tool shaft.

Tools including the embodiments described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture," U.S. Pat. No. 9,295,524 (filed May 31, 2013) to Schena et al., entitled "Redundant Axis and Degree of Freedom for Hardware-Constrained Remote Center Robotic Manipulator" and U.S. Pat. No. 8,852,208 (filed Aug. 12, 2010) to Gomez et al., entitled "Surgical System Instrument Mounting," each of which is hereby incorporated by reference in its entirety. Further, the embodiments described herein may be used, for example, with a da Vinci® Surgical System, such as the da Vinci Si® Surgical System (model no. IS3000) or the da Vinci Xi® Surgical System (model no. IS4000), both with or without Single-Site® single orifice surgery technology, all commercialized by Intuitive Surgical, Inc. of Sunnyvale, California. Although various embodiments described herein are discussed with regard to surgical instruments used with a manipulating system of a teleoperated surgical system, the present disclosure is not limited to use with surgical instruments for a teleoperated surgical system. For example, various embodiments described herein can optionally be used in conjunction with hand-held, manual surgical instruments, or other surgical and non-surgical tools.

Figure 7:
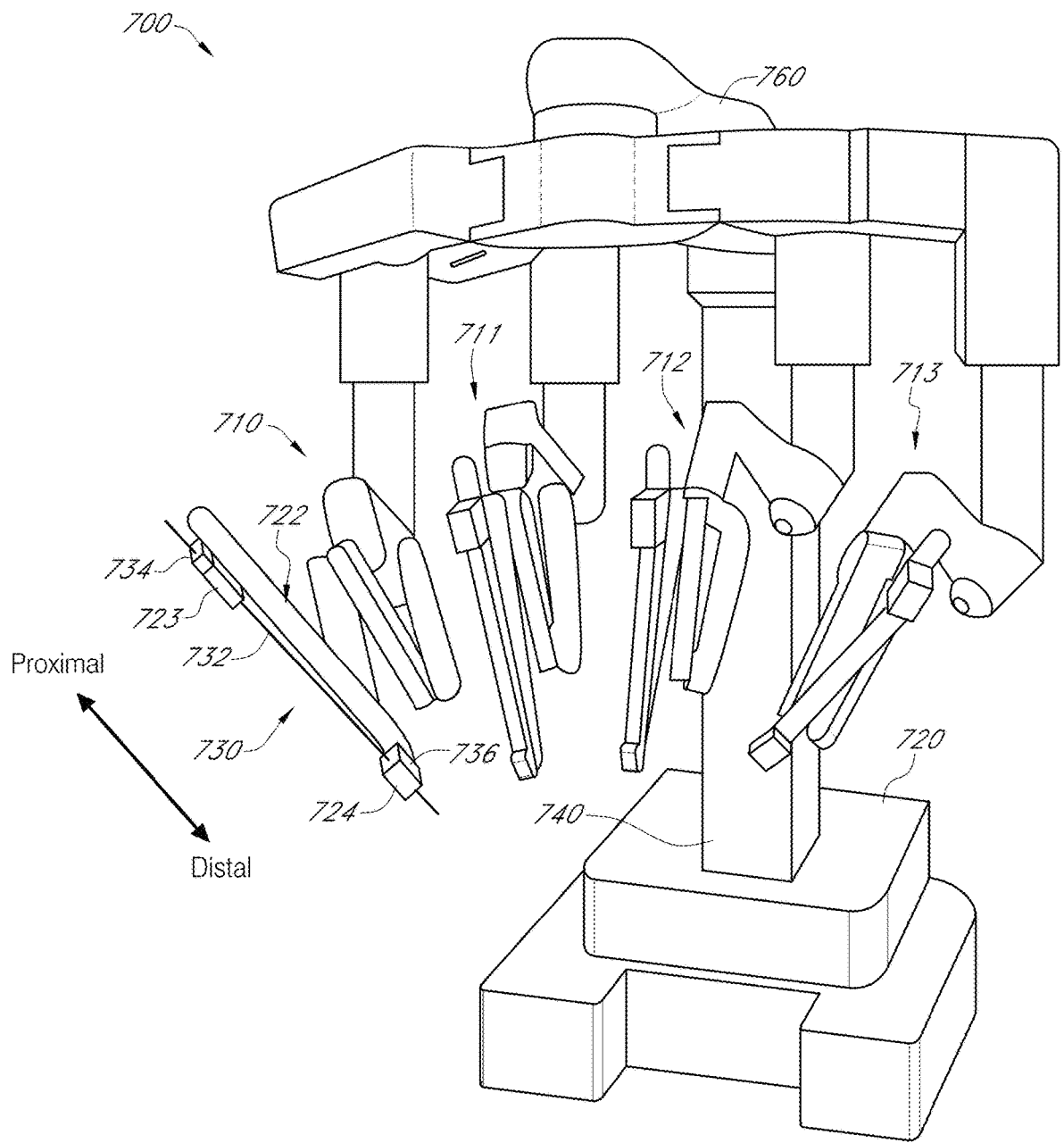
FIG. 7 is a perspective view of a manipulating system according to an embodiment of the present disclosure.

As discussed above, in accordance with various embodiments, surgical instruments of the present disclosure are configured for use in teleoperated, computer-assisted surgical systems (sometimes referred to as robotic surgical systems). Referring now to FIG. 7, an embodiment of a manipulating system 700 of a teleoperated, computer-assisted surgical system, to which surgical instruments are configured to be mounted for use, is shown. Such a surgical system may further include a user control system, such as a surgeon console (not shown) for receiving input from a user to control instruments of manipulating system 700, as well as an auxiliary system, such as a control/vision cart (not shown), as described in, for example, U.S. Pat. Nos. 9,358,074 and 9,295,524, incorporated above.

As shown in the embodiment of FIG. 7, a manipulating system 700 includes a base 720, a main column 740, and a main boom 760 connected to main column 740. Manipulating system 700 also includes a plurality of arms 710, 711, 712, 713, which are each connected to main boom 760. Arms 710, 711, 712, 713 each include an instrument mount portion 722 to which an instrument 730 may be mounted, which is illustrated as being attached to arm 710. Portions of arms 710, 711, 712, 713 may be manipulated during a surgical procedure according to commands provided by a user at the surgeon console. In an embodiment, signal(s) or input(s) transmitted from a surgeon console are transmitted to the control/vision cart, which may interpret the input(s) and generate command(s) or output(s) to be transmitted to the manipulating system 700 to cause manipulation of the instrument 730 (only one such instrument being mounted in FIG. 7) and/or portions of arm 710 to which the instrument 730 is coupled at the manipulating system 700.

Instrument mount portion 722 comprises a drive assembly 723 and a cannula mount 724, with a force transmission mechanism 734 of the instrument 730 connecting with the drive assembly 723, according to an embodiment. Cannula mount 724 is configured to hold a cannula 736 through which a shaft 732 of instrument 730 may extend to a surgery site during a surgical procedure. drive assembly 723 contains a variety of drive and other mechanisms that are controlled to respond to input commands at the surgeon console and transmit forces to the force transmission mechanism 734 to actuate the instrument 730, as those skilled in the art are familiar with.

Although the embodiment of FIG. 7 shows an instrument 730 attached to only arm 710 for ease of viewing, an instrument may be attached to any and each of arms 710, 711, 712, 713. An instrument 730 may be a surgical instrument with an end effector as discussed herein. A surgical instrument with an end effector may be attached to and used with any of arms 710, 711, 712, 713. The embodiments described herein are not limited to the embodiment of FIG. 7 and various other teleoperated, computer-assisted surgical system configurations may be used with the embodiments described herein.

Figure 8:
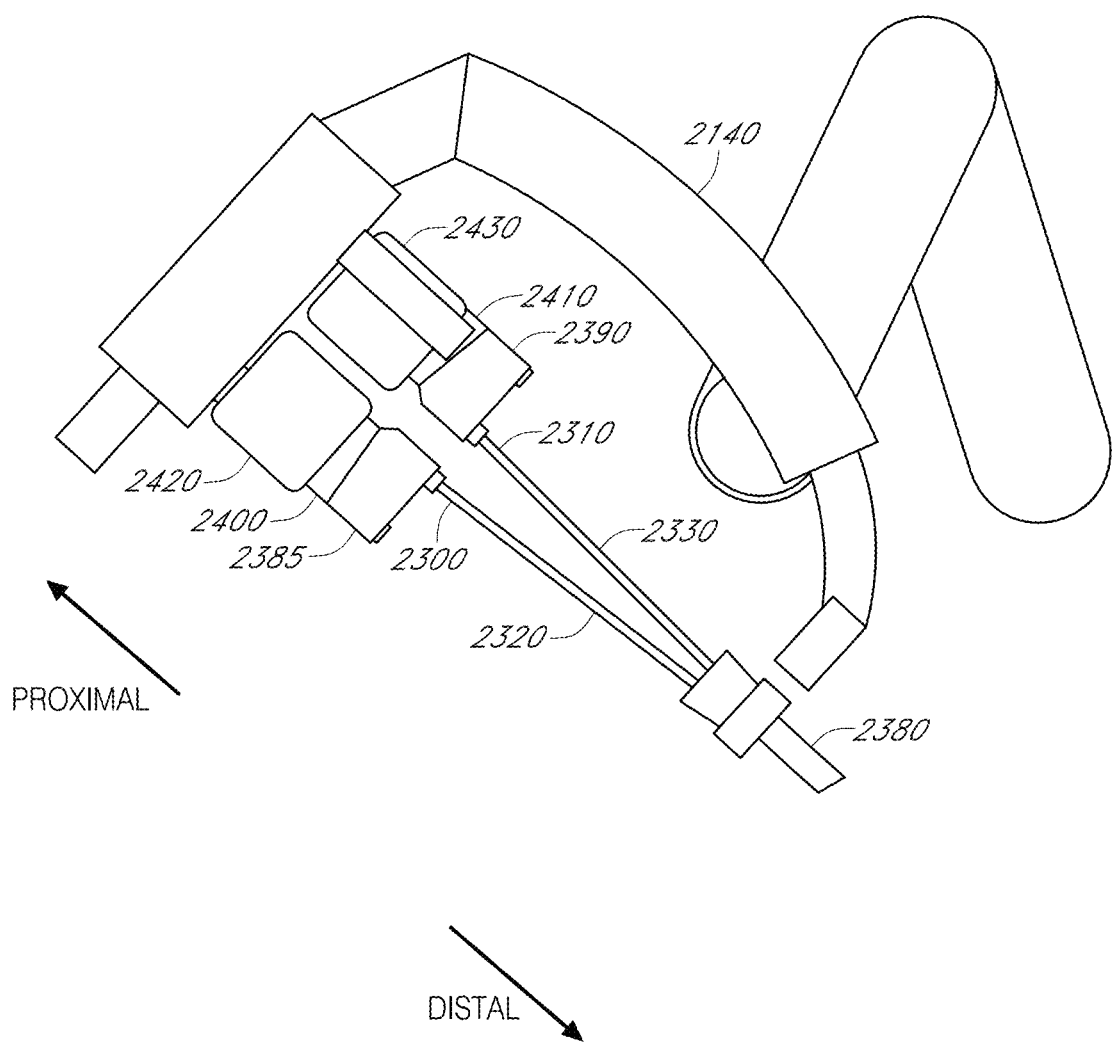
FIG. 8 is a partial schematic view of an embodiment of a manipulator arm of a manipulating system according to the present disclosure with two instruments in an installed position.

Other configurations of surgical systems, such as surgical systems configured for single-port surgery, are also contemplated. For example, with reference now to FIG. 8, a portion of an embodiment of a manipulator arm 2140 of a manipulating system with two surgical instruments 2300, 2310 in an installed position is shown. For example, the embodiments described herein may be used with a da Vinci SPR Surgical System (model no. IS1098), commercialized by Intuitive Surgical, Inc. of Sunnyvale, California. A teleoperated robotic surgical system, including a manipulating system comprising manipulator arm 2140, may be configured according to the embodiments described in U.S. Patent App. Pub. No. US 2014/0128886 A1 (filed No. 1, 2013), to Holop et al. and titled "Flux disambiguation for teleoperated surgical systems," the disclosure of which is incorporated by reference herein. The schematic illustration of FIG. 8 depicts only two surgical instruments for simplicity, but more than two surgical instruments may be received in an installed position at a manipulating system as those having ordinary skill in the art are familiar with. Each surgical instrument 2300, 2310 includes an instrument shaft 2320, 2330 that at a distal end has a moveable end effector or an endoscope, camera, or other sensing device, and may or may not include a wrist mechanism (not shown) to control the movement of the distal end.

In the embodiment of FIG. 8, the distal end portions of the surgical instruments 2300, 2310 are received through a single port structure 2380 to be introduced into the patient. As shown, the port structure includes a cannula and an instrument entry guide inserted into the cannula. Individual instruments are inserted into the entry guide to reach a surgical site. Other configurations of manipulating systems that can be used in conjunction with the present disclosure can use several individual manipulator arms. In addition, individual manipulator arms may include a single instrument or a plurality of instruments. Further, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 2385, 2390 are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate instruments 2300, 2310. The diameter or diameters of an instrument shaft, wrist mechanism, and end effector are generally selected according to the size of the cannula with which the instrument will be used and depending on the surgical procedures being performed. In various embodiments, a shaft and/or wrist mechanism has a diameter of about 4 mm, 5 mm, or 8 mm in diameter, for example, to match the sizes of some existing cannula systems.

This description and the accompanying drawings that illustrate embodiments should not be taken as limiting. Various mechanical, compositional, structural, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements.

Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A tool, comprising:
a transmission mechanism, a shaft, and a rotary device,
wherein the shaft is rotatable with reference to the transmission mechanism through a defined range of rotational motion about a first axis of rotation and comprises a protrusion extending from the shaft in a direction normal to the first axis of rotation; and
the rotary device comprising:
a first stop surface,
a second stop surface,
a notch between the first stop surface and the second stop surface, the notch being configured to receive the protrusion extending from the shaft,
a first profiled portion between the first stop surface and the notch, and
a second profiled portion between the second stop surface and the notch,
wherein each of the first and second profiled portions has a profile complementary to a profile of the shaft; and
wherein rotation of the shaft through a midpoint of the defined range of rotational motion causes the protrusion to enter the notch of the rotary device and rotate the rotary device from a first position to a second position.

2. The tool of claim 1, wherein in the first position of the rotary device, the shaft is prevented from rotating in a first direction beyond a first orientation at which the protrusion contacts the first stop surface.

3. The tool of claim 1, wherein in the second position of the rotary device, the shaft is prevented from rotating in a second direction beyond a second orientation at which the protrusion contacts the second stop surface.

4. The tool of claim 1, wherein the rotary device is rotatable about a second axis of rotation parallel to and offset from the first axis of rotation.

5. The tool of claim 1, wherein the rotary device is rotatable about a second axis of rotation normal to the first axis of rotation.

6. A tool, comprising:
a transmission mechanism comprising:
a capstan,
a pulley coupled to the shaft, and
at least one drive cable operably coupled to the pulley and the capstan;
a shaft rotatable with reference to the transmission mechanism through a defined range of rotational motion about a first axis of rotation and comprises a protrusion extending from the shaft in a direction normal to the first axis of rotation; and
a rotary device comprising:
a first stop surface,
a second stop surface, and
a notch between the first stop surface and the second stop surface,
wherein the notch is configured to receive the protrusion extending from the shaft; and
wherein rotation of the shaft through a midpoint of the defined range of rotational motion causes the protrusion to enter the notch of the rotary device and rotate the rotary device from a first position to a second position.

7. The tool of claim 6, wherein the transmission mechanism is configured to be operably coupled with a manipulator configured to impart rotation to the capstan.

8. The tool of claim 6, wherein the at least one drive cable comprises a first end fixedly coupled to one of the capstan and the pulley and a second end fixedly coupled to the other of the capstan and the pulley.

9. The tool of claim 6, wherein the at least one drive cable comprises two drive cables.

10. The tool of claim 1, wherein the defined range of rotational motion between the first position and the second position is more than 360 degrees.

11. The tool of claim 10, wherein the defined range of rotational motion between the first position and the second position is at least 540 degrees.

12. The tool of claim 10, wherein the defined range of rotational motion between the first position and the second position is at least 630 degrees.

13. The tool of claim 1, wherein the first profiled portion contacts the shaft when the rotary device is rotated from the first position to the second position.

14. The tool of claim 1, wherein rotation of the shaft through the midpoint of the defined range of rotational motion causes the protrusion to enter the notch of the rotary device and rotate the rotary device from the first position to a third position.

15. The tool of claim 14, wherein the second profiled portion contacts the shaft when the rotary device is rotated from the first position to the third position.

* * * * *

UNITED STATES PATENT AND TRADEMARK OFFICE
CERTIFICATE OF CORRECTION

PATENT NO.        : 12,257,700 B2
APPLICATION NO.   : 18/318360
DATED             : March 25, 2025
INVENTOR(S)       : Grant M. Kadokura and Andrew C. Waterbury Page 1 of 1

It is certified that error appears in the above-identified patent and that said Letters Patent is hereby corrected as shown below:

In the Claims

Column 12, Claim 6, Line 9, delete "comprises".

Signed and Sealed this
Fifteenth Day of July, 2025

Coke Morgan Stewart
*Acting Director of the United States Patent and Trademark Office*